(12) United States Patent
Jung

(10) Patent No.: US 10,940,230 B2
(45) Date of Patent: Mar. 9, 2021

(54) CHITOSAN-BASED HEMOSTATIC MEMBER FOR CERVIX AND METHOD OF MANUFACTURING THE SAME

(71) Applicants: ENDOVISION CO., LTD., Daegu (KR); Min Ho Jung, Daegu (KR)

(72) Inventor: Min Ho Jung, Daegu (KR)

(73) Assignees: ENDOVISION CO., LTD., Daegu (KR); Min Ho Jung, Daegu (KR)

( * ) Notice: Subject to any disclaimer, the term of this patent is extended or adjusted under 35 U.S.C. 154(b) by 326 days.

(21) Appl. No.: 15/771,230

(22) PCT Filed: Nov. 14, 2017

(86) PCT No.: PCT/KR2017/012825
§ 371 (c)(1),
(2) Date: Apr. 27, 2018

(87) PCT Pub. No.: WO2019/066131
PCT Pub. Date: Apr. 4, 2019

(65) Prior Publication Data
US 2019/0099512 A1     Apr. 4, 2019

(30) Foreign Application Priority Data

Sep. 29, 2017  (KR) .......................... 10-2017-0127526

(51) Int. Cl.
*A61L 15/28* (2006.01)
*A61F 13/36* (2006.01)
(Continued)

(52) U.S. Cl.
CPC ........ *A61L 15/28* (2013.01); *A61B 17/12131* (2013.01); *A61F 13/00008* (2013.01);
(Continued)

(58) Field of Classification Search
CPC ...... A61L 24/08; A61L 15/28; A61L 2400/04; A61L 24/0036; A61B 17/12131;
(Continued)

(56) References Cited

U.S. PATENT DOCUMENTS 5,836,970 A  *  11/1998  Pandit ................... A61L 15/225
                                                    606/213
2005/0058694 A1* 3/2005  Nielsen ................... A61L 15/28
                                                    424/445

FOREIGN PATENT DOCUMENTS

KR       20010097226 A  * 11/2001
KR         101517112 B1  *  5/2015
KR         10-1700107 B1    1/2017

OTHER PUBLICATIONS

English Translation of KR20010097226 2001; 6 pages. (Year: 2001).*
English translation of KR101517112 2015; 5 pages. (Year: 2015).*

* cited by examiner

*Primary Examiner* — Ernst V Arnold
(74) *Attorney, Agent, or Firm* — Stein IP, LLC

(57) ABSTRACT

This invention relates to a hemostatic member using chitosan having superior hemostatic activity, and more particularly to a chitosan-based hemostatic member for the cervix, suitable for use through insertion into an affected part upon cervical biopsy or surgery, configured to include a hemostatic pack having a projection at an upper end thereof through tying with a thread so as to form a spherical shape using chitosan nonwoven fabrics having a hemostatic function, wherein the thread contains an X-ray-sensitive material, thereby realizing effective hemostasis of the affected part upon cervical biopsy or surgery.

9 Claims, 7 Drawing Sheets

(51) Int. Cl.
*A61B 17/12* (2006.01)
*A61F 13/00* (2006.01)
*A61L 24/00* (2006.01)
*A61L 24/08* (2006.01)
A61B 90/00 (2016.01)
A61B 17/00 (2006.01)
A61B 17/42 (2006.01)

(52) U.S. Cl.
CPC .......... *A61F 13/36* (2013.01); *A61L 24/0036* (2013.01); *A61L 24/08* (2013.01); A61B 2017/00526 (2013.01); A61B 2017/12004 (2013.01); A61B 2017/4225 (2013.01); A61B 2090/3966 (2016.02); A61L 2400/04 (2013.01)

(58) Field of Classification Search
CPC ........... A61B 2017/00526; A61B 2017/12004; A61B 2017/4225; A61B 2090/3966; A61F 13/00008; A61F 13/36
See application file for complete search history.

CHITOSAN-BASED HEMOSTATIC MEMBER FOR CERVIX AND METHOD OF MANUFACTURING THE SAME

CROSS-REFERENCE TO RELATED APPLICATIONS

This application is a national stage of International Application No. PCT/KR2017/012825, filed Nov. 14, 2017, which claims the benefit of priority Korean Application No. 10-2017-0127526, filed Sep. 29, 2017, in the Korean Intellectual Property Office, the disclosures of which are incorporated herein by reference.

BACKGROUND OF THE INVENTION

1. Technical Field

The present invention relates to a hemostatic member using chitosan having superior hemostatic activity, and more particularly to a chitosan-based hemostatic member for the cervix, suitable for effective hemostasis of the affected part upon cervical biopsy or surgery, and a method of manufacturing the same.

2. Description of the Related Art

In the case where an external wound is generated on the body, if the wound is not deep, blood coagulation is achieved through the coagulation mechanism of the blood by a simple measure. However, in the case where the wound is deep or the tissue is stripped for surgery or examination, there is a great need to perform artificial hemostasis of the affected part in order to prevent excessive bleeding.

A conventional technique with regard to the present invention is known to be Korean Patent No. 10-1700107, entitled "Chitosan-based hemostatic dressing and Method of manufacturing the same", filed and registered by the present applicant.

The conventional chitosan-based hemostatic dressing includes a chitosan dressing composed of 100% chitosan material and involved in hemostasis and repair of a wound or surgical site when applied to the wound or surgical site of the human body, with a predetermined size and shape, and an auxiliary member formed on at least one surface of the chitosan dressing and configured to prevent fiber detachment and maintain the shape of the chitosan dressing. The chitosan dressing includes at least one X-ray-sensitive material so as to enable determination of the position of the dressing using an X-ray detector when applied to the inside of the human body and sutured.

Chitosan is a natural substance known to have hemostatic activity and antibacterial and antiviral effects, and is a kind of polysaccharide, which is a compound obtained by deacetylating chitin contained in the shells of crabs and shrimps, the bones of squids, cell walls of microorganisms such as fungi and bacteria, and the like. It has been used in a variety of industrial fields since the mid 1980s.

The main use of such chitosan is in the wastewater disposal fields, including coagulants, heavy metal adsorbents, dye wastewater purifying agents, etc., and in the agricultural fields, including soil improvement agents, insecticides, plant antiviral agents, agricultural chemicals, etc. However, as the advantages and various characteristics of chitosan are revealed, the application range thereof is expanding to include application fields of food and beverages, health and hygiene, cosmetics, textiles, and medicine.

Particularly, chitosan has been receiving attention as a medical material since the 1990s, and is thus utilized for a wound-healing agent, artificial skin, an embolic agent, a blood coagulant, an artificial kidney membrane, a biodegradable surgical suture, and an antibacterial material.

The related art is to provide a hemostatic dressing, which may be generally utilized based on the efficient activity of chitosan. The dressing in the related art may be effectively employed for hemostasis of the external skin of the body, exposed to the outside, but limitations are imposed on hemostasis using such a general dressing upon the surgery or treatment of the body organs forming the special structure and shape inside the body.

The present invention focuses on effective hemostasis of the affected part that occurs when the woman undergoes surgery or diagnostic biopsy for cervical cancer. To this end, there is required a hemostatic member capable of achieving effective hemostasis of the corresponding affected part, rather than a gauze-like form that may be generally used, as in the related art.

SUMMARY OF THE INVENTION

Accordingly, the present invention has been made keeping in mind the problems encountered in the related art, and the present invention is intended to provide a chitosan-based hemostatic member for the cervix, which is responsible for effective hemostasis of the corresponding affected part when requiring hemostasis of the cervix upon surgery or biopsy.

In addition, the present invention is intended to provide a method of manufacturing the chitosan-based hemostatic member for the cervix.

Therefore, an aspect of the present invention provides a chitosan-based hemostatic member for the cervix, suitable for use through insertion into the affected part upon cervical biopsy or surgery, configured to include a hemostatic pack having a projection at the upper end thereof through tying with a thread so as to form a spherical shape using chitosan nonwoven fabrics having a hemostatic function, the thread containing an X-ray-sensitive material.

Preferably, the outer surface of the hemostatic pack is coated with a CMCS (Carboxymethyl chitosan) coating layer.

Preferably, the outer surface of the CMCS coating layer is covered with a CMCS sponge.

Preferably, the outer surface of the hemostatic pack is covered with a CMCS sponge.

Preferably, the CMCS sponge has a thickness ranging from 2 mm to 10 mm.

Another aspect of the present invention provides a chitosan-based hemostatic member for the cervix, configured to include a hemostatic pack having a projection at an upper end thereof through tying with a thread so as to form a spherical shape using chitosan nonwoven fabrics having a hemostatic function, wherein peripheral pressing portions are formed by connecting a typical nonwoven fabric or a chitosan nonwoven fabric in the form of a straight line to both sides of the projection, and the thread containing an X-ray-sensitive material extends for connection to the peripheral pressing portions.

Preferably, the thread connected to the peripheral pressing portions extends by passing through each of the peripheral pressing portions from inside the hemostatic pack.

In addition, the present invention provides a method of manufacturing a chitosan-based hemostatic member for the cervix, comprising: preparing chitosan nonwoven fabrics composed of chitosan fibers; and shaping a hemostatic pack having a spherical shape by stacking the chitosan nonwoven fabrics and subjecting the edges thereof to gathering together and tying with a thread containing an X-ray-sensitive material so as to form a projection.

Preferably, the method comprises, after the shaping the hemostatic pack: forming a CMCS coating layer on the surface of the hemostatic pack by immersing the hemostatic pack in a CMCS solution; and then forming a CMCS sponge by covering the outer surface of the CMCS coating layer with the CMCS solution.

Preferably, the forming the CMCS sponge comprises: seating the hemostatic pack having the CMCS coating layer formed thereon in a shaping mold; introducing the CMCS solution into the shaping mold; lyophilizing the CMCS solution by placing the shaping mold in a lyophilizer to thus achieve an integration with the hemostatic pack; and thermally treating a lyophilized body by applying heat thereto.

Preferably, preliminary freezing is performed before the lyophilizing, and the preliminary freezing is carried out in a manner in which the shaping mold is stabilized at 0--5° C. for 1-2 hr and then immersed for 15 min to 30 min in ethanol cooled to −80° C. or less and thus instantly treated.

Preferably, the preliminary freezing is carried out in a manner in which the shaping mold is placed in the lyophilizer, stabilized in a supercooled state at 0° C.--5° C. for 2-3 hr, and then treated at −30° C.--40° C. for 3-4 hr.

Preferably, the CMCS solution is prepared by dissolving 3-5% CMCS in distilled water, adding 1-3% glycerin thereto, and performing stirring for 2 hr or more.

Preferably, the CMCS solution obtained through stirring is filtered using a mesh filter so as to increase purity, and is stored at 2-4° C. so as to be defoamed.

According to the present invention, a chitosan-based hemostatic member for the cervix has the effect of preventing a patient from being in danger due to excessive bleeding by performing effective hemostasis of the specific affected part.

Also, according to the present invention, the chitosan-based hemostatic member is provided in a shape that is the most suitable for the specific affected part, and can thus be applied directly to the affected part without any pretreatment, thereby increasing the convenience of medical staff.

Also, according to the present invention, the hemostatic member is configured such that peripheral pressing portions are provided at both sides of a hemostatic pack, thereby realizing more effective hemostasis of the affected part.

Also, according to the present invention, the hemostatic member is configured to include a thread containing an X-ray-sensitive material, and thus, even when the hemostatic member is not removed from the body due to user error, the position thereof can be easily determined and thus the subsequent procedure can be performed.

DESCRIPTION OF SPECIFIC EMBODIMENTS

Hereinafter, a detailed description will be given of a chitosan-based hemostatic member for the cervix and a method of manufacturing the same according to the present invention, with reference to the drawings appended in order to aid the understanding of the technical spirit of the present invention. It should be pointed out that the drawings and the description of the preferred embodiments are merely illustrative examples based on the technical spirit of the present invention, and that the technical scope of the present invention is not limited thereto.

Figure 1:
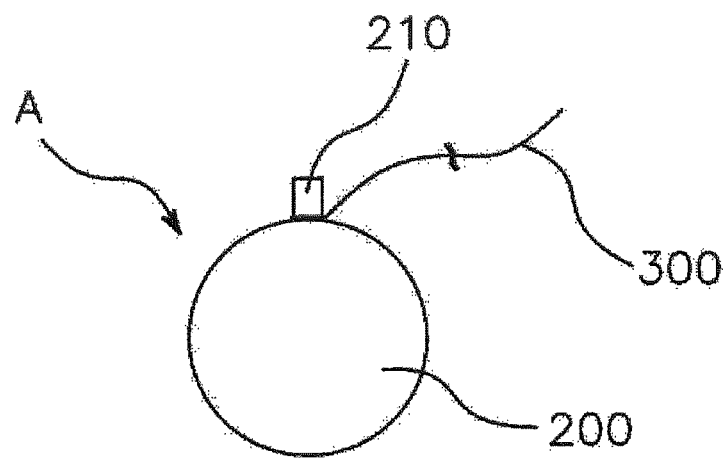
FIG. 1 conceptually shows a chitosan-based hemostatic member for the cervix according to a preferred first embodiment of the present invention.
Figure 2:
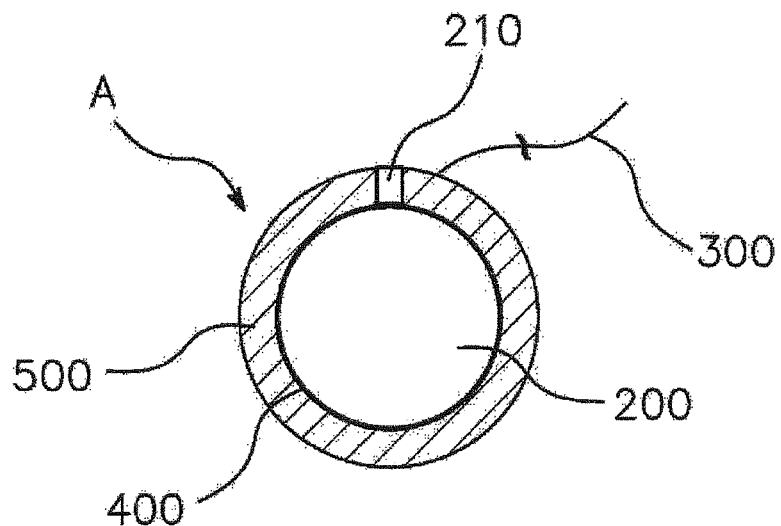
FIG. 2 conceptually shows a chitosan-based hemostatic member for the cervix according to a second embodiment of the present invention.
Figure 3:
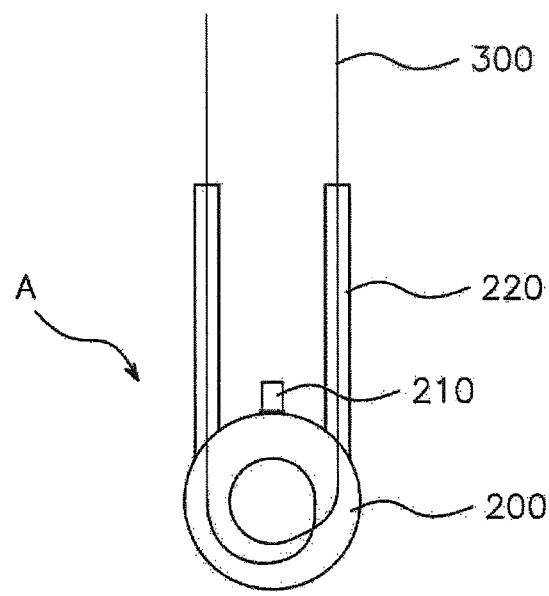
FIG. 3 conceptually shows a chitosan-based hemostatic member for the cervix according to a third embodiment of the present invention.
Figure 4:
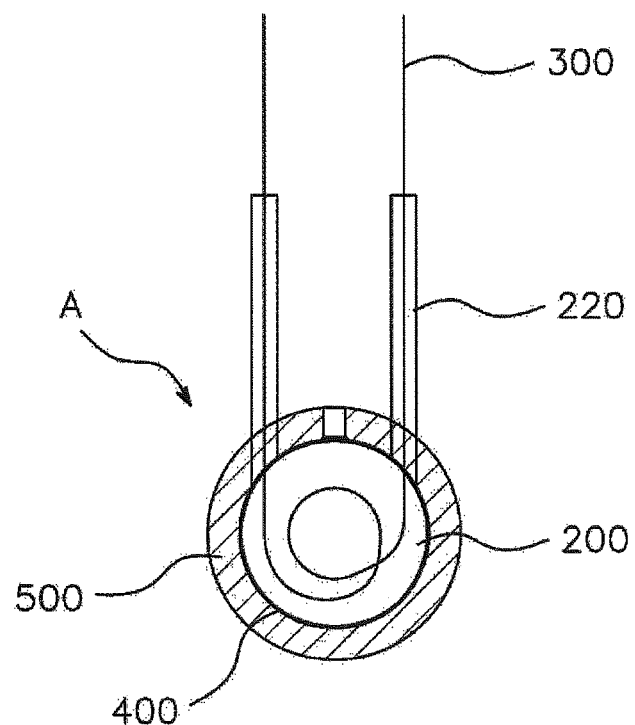
FIG. 4 conceptually shows a chitosan-based hemostatic member for the cervix according to a fourth embodiment of the present invention.
Figure 5:
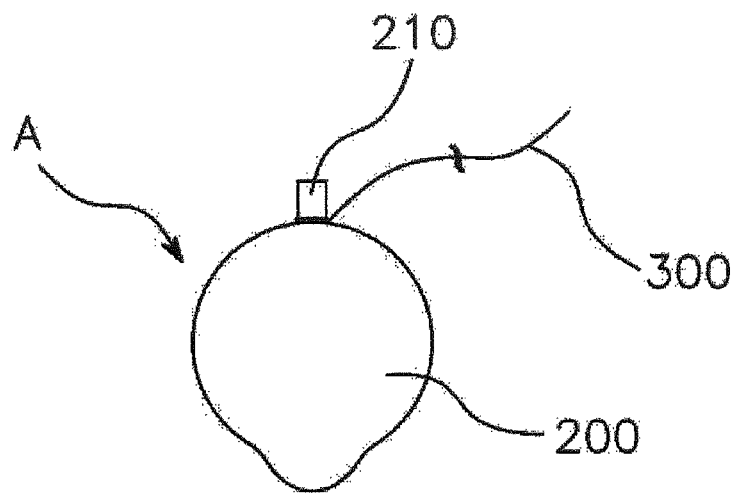
FIG. 5 conceptually shows a hemostatic member according to a fifth embodiment of the present invention.
Figure 6:
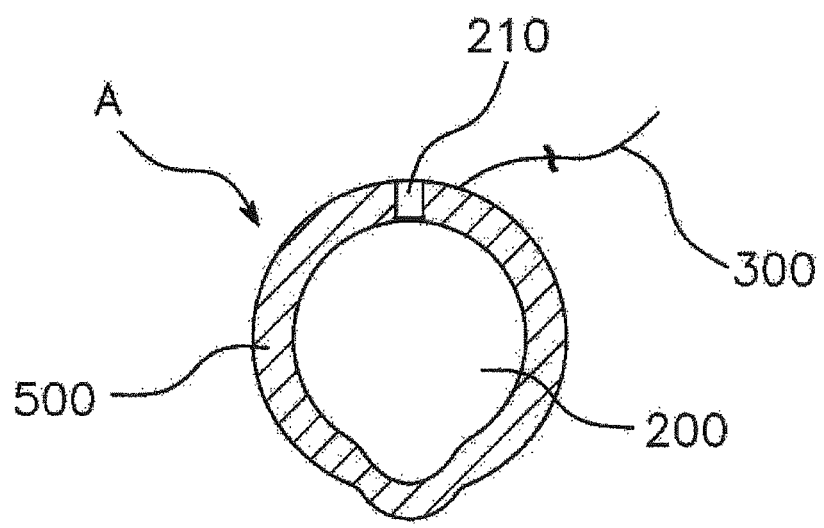
FIG. 6 conceptually shows a hemostatic member according to a sixth embodiment of the present invention.
Figure 7:
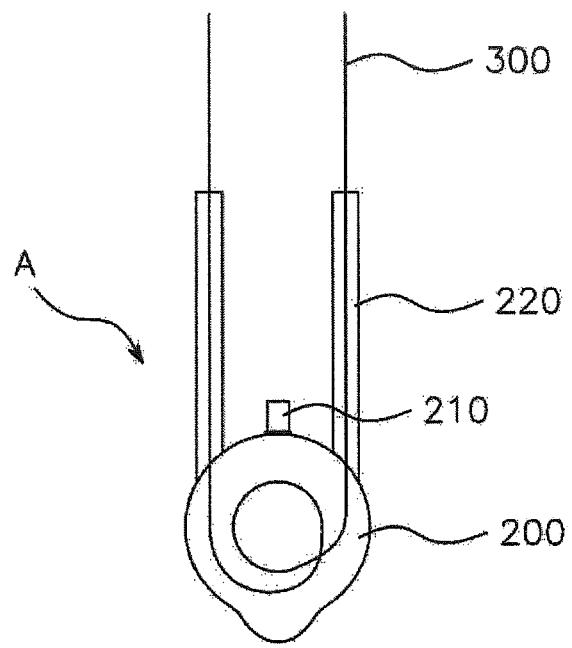
FIG. 7 conceptually shows a hemostatic member according to a seventh embodiment of the present invention.
Figure 8:
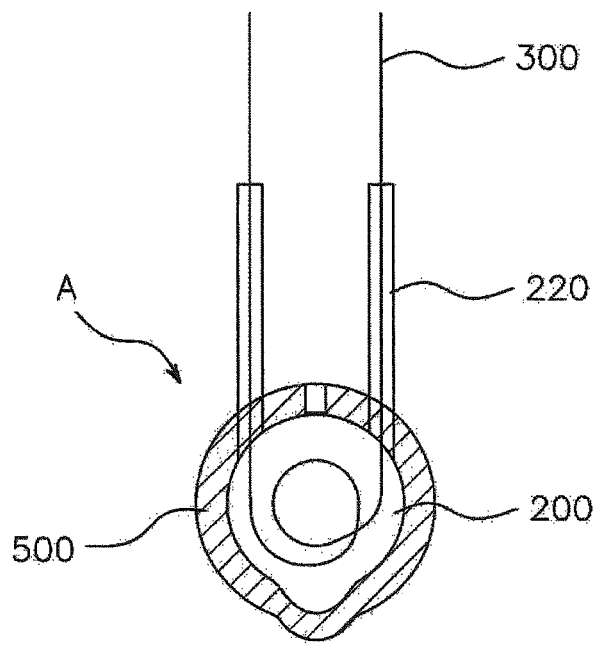
FIG. 8 conceptually shows a hemostatic member according to an eighth embodiment of the present invention.
Figure 9:
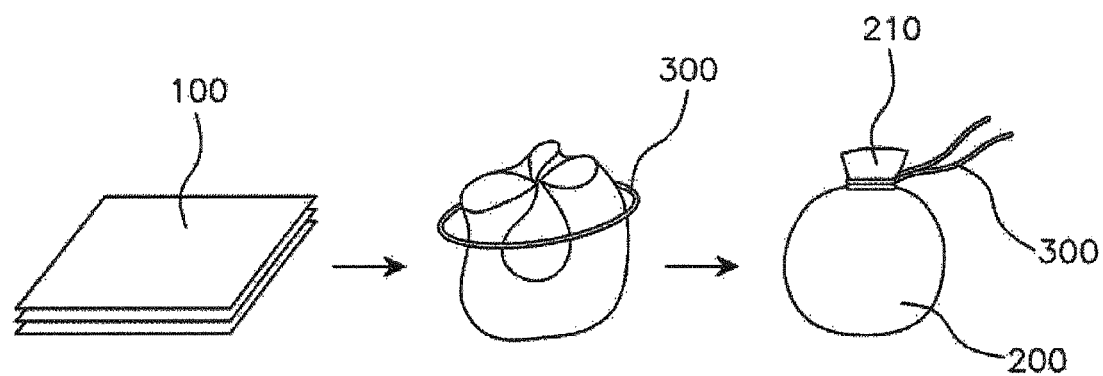
FIG. 9 shows the formation of a hemostatic pack using chitosan nonwoven fabrics.
Figure 10:
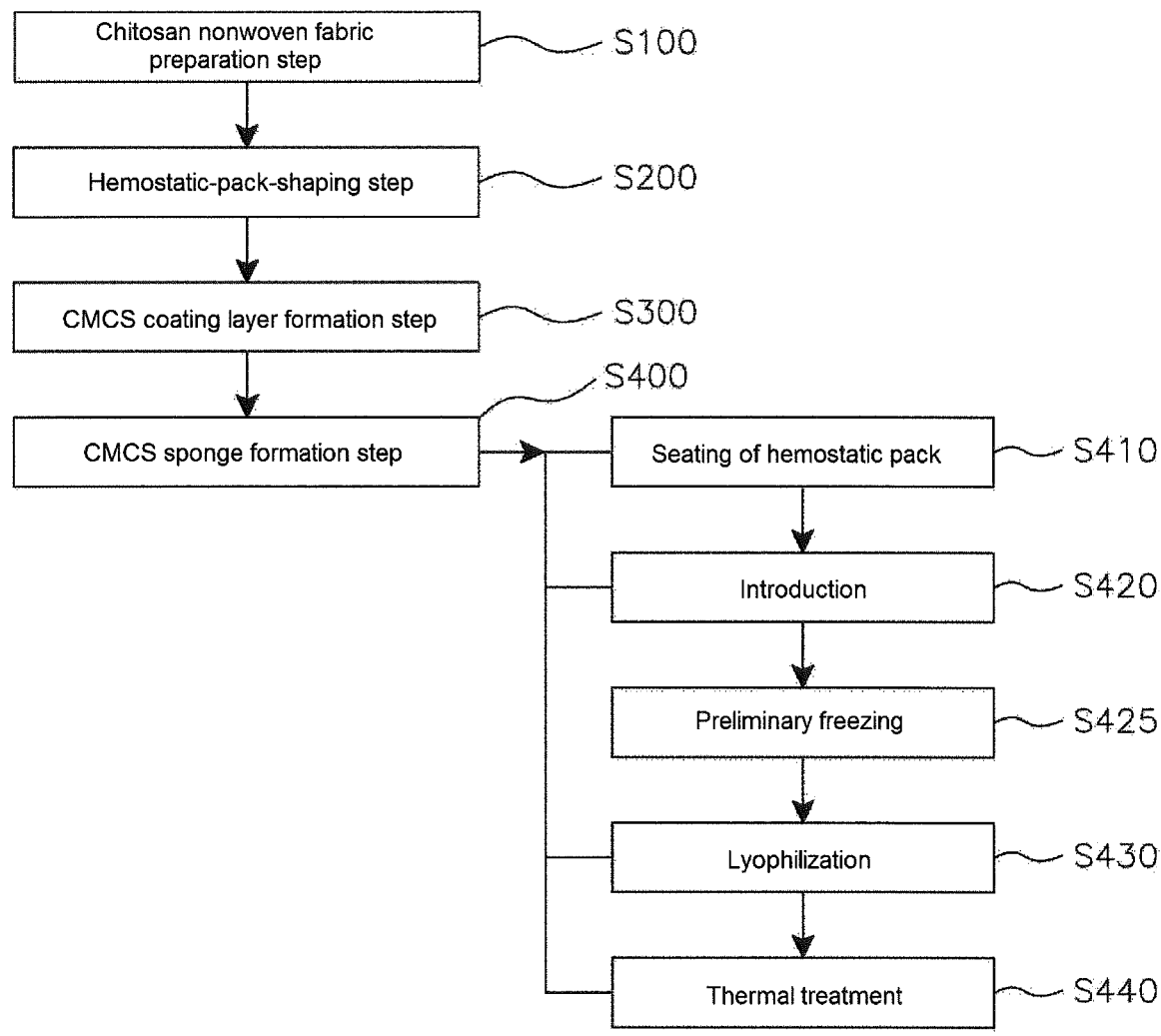
FIG. 10 shows the process of manufacturing the chitosan-based hemostatic member for the cervix.
Figure 11:
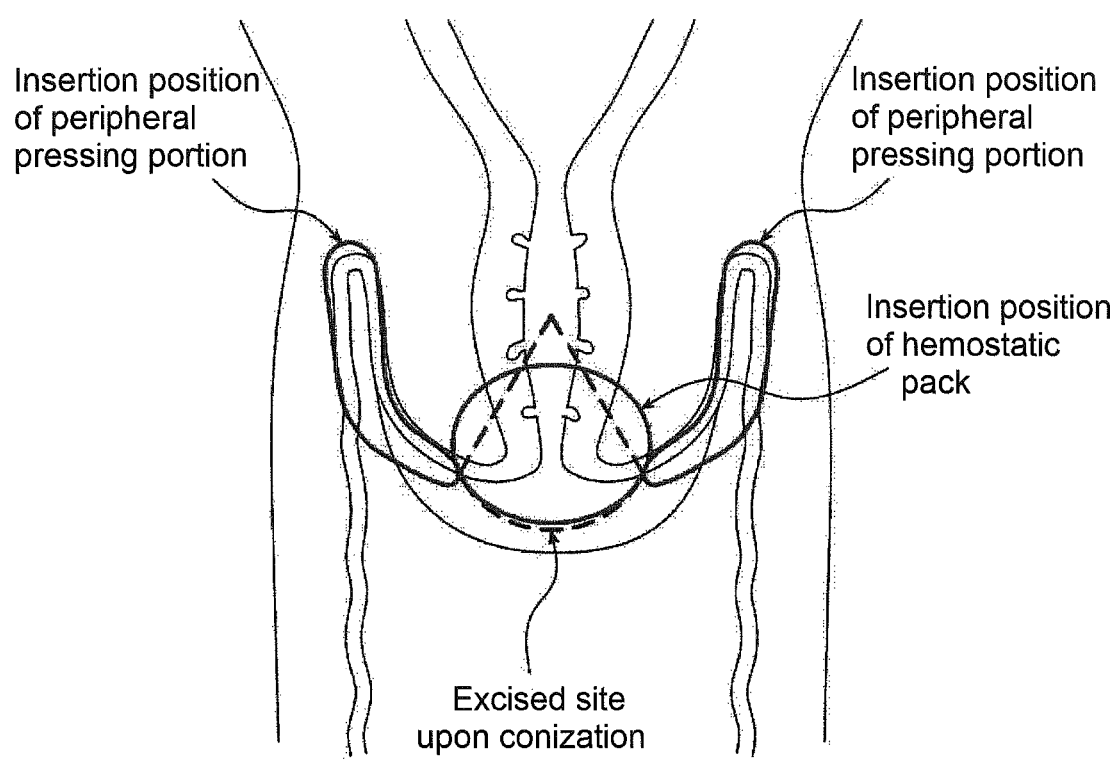
FIG. 11 shows the actual use of the hemostatic member according to the present invention.

FIG. 1 conceptually shows a chitosan-based hemostatic member for the cervix according to a preferred first embodiment of the present invention, FIG. 2 conceptually shows a chitosan-based hemostatic member for the cervix according to a second embodiment of the present invention, FIG. 3 conceptually shows a chitosan-based hemostatic member for the cervix according to a third embodiment of the present invention, FIG. 4 conceptually shows a chitosan-based hemostatic member for the cervix according to a fourth embodiment of the present invention, FIG. 5 conceptually shows a hemostatic member according to a fifth embodiment of the present invention, FIG. 6 conceptually shows a hemostatic member according to a sixth embodiment of the present invention, FIG. 7 conceptually shows a hemostatic member according to a seventh embodiment of the present invention, FIG. 8 conceptually shows a hemostatic member according to an eighth embodiment of the present invention, FIG. 9 shows the formation of a hemostatic pack using chitosan nonwoven fabrics, FIG. 10 shows the process of manufacturing the chitosan-based hemostatic member for the cervix, and FIG. 11 shows the actual use of the hemostatic member according to the present invention.

As shown in the drawings, the chitosan-based hemostatic member for the cervix (which is hereinafter referred to as a hemostatic member) according to the present invention is used by being inserted into the affected part upon cervical biopsy or surgery.

As seen in FIGS. 1 and 9, the hemostatic member A includes a hemostatic pack 200 formed of chitosan nonwoven fabrics 100, and the hemostatic pack is provided in a spherical shape using the chitosan nonwoven fabrics 100. In order to form a sphere like a ball, the edges of chitosan nonwoven fabrics 100 are gathered together and tied with a thread 300 to thus form a projection 210 at the upper end of the hemostatic pack.

Also, the thread 300 used to make the projection 210 is composed of a yarn containing an X-ray-sensitive material.

The chitosan nonwoven fabrics 100 are composed of fibers containing chitosan, and may exhibit superior hemostatic activity by virtue of the chitosan.

The chitosan nonwoven fabrics 100 are stacked, and the edges thereof are gathered together and tied with the thread 300, thereby forming a hemostatic pack 200 having a spherical shape.

The hemostatic member A including the hemostatic pack 200 having a spherical shape formed using the chitosan nonwoven fabrics 100 may be inserted into the affected part.

More preferably, as shown in FIG. 2, a CMCS (Carboxymethyl chitosan) coating layer 400 may be formed on the outer surface of the hemostatic pack 200.

CMCS has strong ability to absorb blood and functions to coat the affected part and is thus more effective at hemostasis. Also, CMCS has high biocompatibility and high biodegradability and is nontoxic.

Although the CMCS coating layer 400 may be provided thinly on the outer surface of the hemostatic pack 200, it is more preferred that the outer surface of the CMCS coating layer 400 be covered with a CMCS sponge 500.

Unlike the CMCS coating layer 400, the CMCS sponge 500 has a considerable thickness, and the hemostatic pack 200 is first coated with the CMCS coating layer 400 and the CMCS sponge 500 is then formed thereon, whereby the CMCS sponge 500 may be provided at a predetermined thickness while covering the CMCS coating layer 400 without the inflow of liquid CMCS solution into the hemostatic pack 200.

In order to form the CMCS coating layer 400 or the CMCS sponge 500, the CMCS solution is prepared and used. When the CMCS coating layer 400 is formed thinly on the hemostatic pack 200, the hemostatic pack 200 is immersed in the CMCS solution, taken out therefrom, and then dried, thereby forming a thin CMCS coating layer 400.

Meanwhile, the hemostatic member may be configured such that the outer surface of the hemostatic pack 200 is directly covered with the CMCS sponge 500. In the case in which the CMCS sponge 500 is formed on the outer surface of the hemostatic pack 200 without the CMCS coating layer, uniformity of the thickness thereof may slightly decrease, but the function as the hemostatic member A may be sufficiently exhibited.

Here, the thickness of the CMCS sponge 500 formed on the outer surface of the hemostatic pack 200 or on the CMCS coating layer 400 preferably falls in the range of about 2-10 mm.

The CMCS sponge 500 is composed of a sponge structure having a predetermined thickness to thus exhibit superior blood absorption performance. When the blood is absorbed thereby, the sponge structure is gelled to thus coat the affected part, whereby hemostasis occurs.

The CMCS sponge 500 has to have a thickness ranging from 2 mm to 10 mm so as to absorb an appropriate amount of blood. If the thickness thereof is less than 2 mm, poor blood absorption performance may result. On the other hand, if the thickness thereof exceeds 10 mm, the size of the hemostatic member A is excessively enlarged, making it difficult to apply it to the affected part.

Meanwhile, the chitosan-based hemostatic member for the cervix according to the present invention may be provided in the forms shown in FIGS. 3 and 4.

In the hemostatic pack 200 having the projection 210 through tying with the thread 300 so as to form a spherical shape using the chitosan nonwoven fabrics 100, peripheral pressing portions 220 may be further formed at both sides of the projection 210, and the thread 300 containing an X-ray-sensitive material may be connected to the peripheral pressing portions 220.

The peripheral pressing portions 220, connected to the hemostatic pack 200, are configured such that a typical nonwoven fabric or a chitosan nonwoven fabric is connected in the form of a long straight line, and the peripheral pressing portions 220 are inserted around the cervix to thus cause pressure inwards for hemostasis, thereby aiding in hemostasis.

Preferably, the thread 300, connected to the peripheral pressing portions 220, extends by passing through the inside of each of the peripheral pressing portions 220 while being twisted from the inside of the hemostatic pack 200.

The thread 300, connected to the peripheral pressing portions 220, contains an X-ray-sensitive material, whereby the position of the hemostatic member A inserted into the human body may be easily determined. When the hemostatic member A is removed after sufficient hemostasis, the hemostatic member A may be easily removed by pulling the tip of the thread 300.

FIGS. 5 to 8 show modifications of the hemostatic pack 200, the lower end of which protrudes.

When the lower end of the hemostatic pack 200 is formed to protrude, the pressure level may be increased upon insertion into the affected part, whereby more efficient hemostasis may be realized.

As shown in the drawings, the modifications of the hemostatic pack 200 may be applied to all of the above first to fourth embodiments.

Next, a method of manufacturing the chitosan-based hemostatic member for the cervix according to the present invention is described below.

FIG. 9 illustrates the formation of a hemostatic pack using chitosan nonwoven fabrics, and FIG. 10 shows the process of manufacturing the hemostatic member according to the present invention.

As shown in the drawings, the method of manufacturing the hemostatic member according to the present invention basically includes a chitosan nonwoven fabric preparation step (S100) and a hemostatic-pack-shaping step (S200).

In the chitosan nonwoven fabric preparation step (S100), chitosan nonwoven fabrics 100 composed of chitosan fibers are prepared.

Subsequently, the hemostatic-pack-shaping step (S200) is performed in order to form a hemostatic pack 200 using the prepared chitosan nonwoven fabrics 100.

In the hemostatic-pack-shaping step (S200), the chitosan nonwoven fabrics 100 are stacked and the edges thereof are gathered together to thus form a projection 210 at the upper end thereof. In order to bind the projection 210, the thread 300 containing an X-ray-sensitive material is used. When the projection 210 for a spherical shape is tied using the thread 300, the hemostatic pack 200 is formed.

After the hemostatic-pack-shaping step (S200), a CMCS coating layer formation step (S300) and a CMCS sponge formation step (S400) are sequentially performed.

In the CMCS coating layer formation step (S300), the hemostatic pack 200 is immersed in a CMCS solution, whereby a CMCS coating layer 400 is formed on the surface of the hemostatic pack 200. The hemostatic pack 200 is immersed in the CMCS solution, taken out therefrom, squeezed and then naturally dried. Here, drying is performed for about 16 hr, whereby the CMCS coating layer 400 is formed thinly on the surface of the hemostatic pack 200.

After the formation of the CMCS coating layer 400 on the surface of the hemostatic pack 200, a CMCS sponge 500 that covers the outer surface of the CMCS coating layer 400 is formed. The CMCS sponge 500 is formed thickly compared to the CMCS coating layer 400, and the CMCS solution is placed in a predetermined shaping mold and fixed so as to form a spherical shape.

The CMCS sponge formation step (S400) is further subdivided into seating of the hemostatic pack (S410), introduction (S420), lyophilization (S430), and thermal treatment (S440).

During the seating of the hemostatic pack (S410), the hemostatic pack 200, which includes the CMCS coating layer 400 formed thereon, is placed in a predetermined shaping mold and fixed.

During the introduction (S420), the CMCS solution is introduced into the shaping mold. When the CMCS solution is added in a predetermined amount to fill the shaping mold, the inside of the shaping mold is filled with the CMCS solution while the CMCS coating layer 400 is covered by the CMCS solution.

The lyophilization (S430) is performed after the introduction of the CMCS solution in the shaping mold, and during the lyophilization (8430), the shaping mold is placed in a lyophilizer, followed by rapid cooling and then lyophilization, whereby water is evaporated and thus a CMCS sponge 500 integrated with the hemostatic pack 200 is formed.

The lyophilization is performed in a manner in which drying is conducted while the temperature is elevated from −40° C. to 30° C. in a vacuum.

After the lyophilization, the hemostatic pack 200, the CMCS coating layer 400, and the CMCS sponge 500 are integrated with each other, thus obtaining a single hemostatic member A.

More preferably, preliminary freezing (S425) is performed before the lyophilization (S430). That is, lyophilization may be conducted after preliminary freezing.

During the preliminary freezing (S425), the temperature is reduced as rapidly as possible, whereby the hemostatic member passes through a maximum ice crystal generation zone of 0--5° C. within a short time to thus prevent ice crystals from forming during the freezing. This is because it helps to uniformly form pores when the sponge structure is formed through the thermal treatment (S440) to be described later. Briefly, the preliminary freezing (S425) may contribute to an improvement in the absorption capability.

More specifically, during the preliminary freezing (S425), the shaping mold is stabilized at 0--5° C. for 1-2 hr, and then immersed in ethanol cooled at an ultralow temperature of −80° C. or less to thus be instantaneously frozen. Preferably, it is immersed for 15 min to 30 min in ethanol cooled to −80° C. or less so that instant freezing occurs, and the ethanol immersion is performed in a cryogenic freezer at −80° C. By rapidly reducing the temperature and passing the hemostatic member through the maximum ice crystal generation zone within a short time, ice crystals do not form, and uniform pore formation may be induced in the subsequent procedure.

The preliminary freezing (S425) may also progress under the following conditions. Another type of preliminary freezing (S425) is characterized by the use of supercooling. Specifically, the shaping mold is placed in a lyophilizer and thus supercooled, followed by rapid freezing (complete freezing in a few seconds), whereby ice crystals do not form during the freezing and uniform pores may be formed upon the production of a sponge structure through the subsequent thermal treatment (S440). In addition, the preliminary freezing (S425) may contribute to an improvement in the absorption capability.

More specifically, the preliminary freezing (S425) is preferably carried out in a manner in which the shaping mold is placed in a lyophilizer, stabilized in a supercooled state at 0° C.--5° C. for 2-3 hr, and treated at −30° C.--40° C. for 3-4 hr.

When the supercooled state is maintained and then instant freezing is conducted in this way, ice crystals do not form and uniform pore formation may be induced in the subsequent procedure.

After the lyophilization (S430), thermal treatment (S440) is carried out. When the lyophilized body is thermally treated by applying predetermined heat thereto, the sponge structure is activated by the crosslinking action to thus increase the blood absorption capability. Here, the thermal treatment (S440) is performed at a temperature of about 70-80° C. for 12-16 hr.

After the thermal treatment (S440), the final hemostatic member A is completed.

Preferably, the CMCS solution is prepared by dissolving 3-5% CMCS in distilled water, adding 1-3% glycerin thereto, and stirring for 2 hr or more.

Here, 3-5% CMCS indicates a mixture comprising 3-5 g of a CMCS powder and 100 ml of distilled water, which are mixed together, and 1-3% glycerin indicates a mixture comprising 1-3 ml of glycerin and 100 ml of distilled water, which are mixed together.

The CMCS solution is prepared by dissolving 3-5% CMCS in distilled water, adding 1-3% glycerin thereto, and stirring for 2 hr or more. More preferably, the CMCS solution obtained through stirring is filtered using a mesh filter so as to maximally increase purity. The high-purity CMCS filtered through a mesh filter is stored at 2-4° C. so as to be defoamed.

FIG. 11 is an illustration of actual use of a chitosan-based hemostatic member for the cervix according to the present invention.

As shown therein, when cervical cancer surgery (conization) is performed, the excision is performed in the shape of a sector as shown in FIG. 11, resulting in a lot of bleeding.

The hemostatic member A according to the present invention is used for hemostasis of the corresponding affected part. The hemostatic member A is inserted and pressed so as to block the excised site by the hemostatic pack 200, whereby bleeding is stopped. Furthermore, when peripheral pressing portions 220 are pushed into both sides of the excised site for efficient pressing, the excised site is pushed inwards and thus comes into close contact with the hemostatic pack 200, thus realizing more efficient hemostasis.

When the hemostatic member A is provided with the CMCS sponge 500, the blood is absorbed into the CMCS sponge 500 and the CMCS sponge 500 becomes gelled to thus coat the affected part, thereby more effectively exhibiting complex functions such as hemostasis and infection prevention.

According to the present invention, the chitosan-based hemostatic member for the cervix and the method of manufacturing the same are suitable for use in hemostasis of the cervix.

What is claimed is:

1. A chitosan-based hemostatic member, comprising: (1) a hemostatic pack made of chitosan nonwoven fabrics formed in a spherical shape and having a projection at an upper end thereof, said projection the result of the chitosan nonwoven fabrics having been tied with a thread; and (2) peripheral pressing portions, wherein the peripheral pressing portions comprise a non-chitosan nonwoven fabric or a chitosan nonwoven fabric in a form of a straight line connected to both sides of the projection, the thread contains an X-ray-sensitive material and extends for connection to the peripheral pressing portions, the nonwoven fabrics have a hemostatic function, and the chitosan-based hemostatic member is suitable for use through insertion into an affected part of a cervix upon cervical biopsy or surgery.

2. The chitosan-based hemostatic member of claim 1, wherein the thread connected to the peripheral pressing portions extends by passing through each of the peripheral pressing portions from inside the hemostatic pack.

3. A method of manufacturing the chitosan-based hemostatic member of claim 1 for a cervix, comprising:

preparing chitosan nonwoven fabrics composed of chitosan fibers; and shaping the hemostatic pack having the spherical shape by stacking the chitosan nonwoven fabrics and subjecting edges thereof to gathering together and tying with the thread containing an X-ray-sensitive material so as to form a projection.

4. The method of claim 3, comprising, after the shaping the hemostatic pack:

forming a CMCS coating layer on a surface of the hemostatic pack by immersing the hemostatic pack in a CMCS solution; and then forming a CMCS sponge by covering an outer surface of the CMOS coating layer with the CMCS solution.

5. The method of claim 4, wherein the forming the CMCS sponge comprises:

seating the hemostatic pack having the CMCS coating layer formed thereon in a shaping mold;

introducing the CMCS solution into the shaping mold;

lyophilizing the CMCS solution by placing the shaping mold in a lyophilizer to thus achieve an integration with the hemostatic pack; and thermally treating a lyophilized body by applying heat thereto.

6. The method of claim 5, wherein preliminary freezing is performed before the lyophilizing, and the preliminary freezing is carried out in a manner in which the shaping mold is stabilized at 0--5° C. for 1-2 hr and then immersed for 15 min to 30 min in ethanol cooled to −80° C. or less and thus instantly treated.

7. The method of claim 5, wherein preliminary freezing is performed before the lyophilizing, and the preliminary freezing is carried out in a manner in which the shaping mold is placed in the lyophilizer and stabilized in a supercooled state at 0° C.--5° C. for 2-3 hr and then treated at −30° C.--40° C. for 3-4 hr.

8. The method of claim 4, wherein the CMCS solution is prepared by dissolving 3-5% CMCS in distilled water, adding 1-3% glycerin thereto, and performing stirring for 2 hr or more.

9. The method of claim 8, wherein the CMCS solution obtained through stirring is filtered using a mesh filter so as to increase purity, and is stored at 2-4° C. so as to be defoamed.

* * * * *